United States Patent
Frieze et al.

(10) Patent No.: US 6,436,357 B1
(45) Date of Patent: Aug. 20, 2002

(54) INSTRUMENT BRACKET FOR USE WITH A STERILIZABLE TRAY

(75) Inventors: Marcia A Frieze, Alpine; Allan S. Frieze, Jersey City, both of NJ (US)

(73) Assignee: Case Medical, Inc., Ridgefield, NJ (US)

(*) Notice: Subject to any disclaimer, the term of this patent is extended or adjusted under 35 U.S.C. 154(b) by 0 days.

(21) Appl. No.: 09/403,399
(22) PCT Filed: Apr. 22, 1997
(86) PCT No.: PCT/US97/06650
§ 371 (c)(1), (2), (4) Date: Oct. 20, 1999
(87) PCT Pub. No.: WO98/47544
PCT Pub. Date: Oct. 29, 1998

(51) Int. Cl.[7] .................................................. A61L 2/00
(52) U.S. Cl. .................... 422/300; 422/292; 422/297; 206/263; 206/363; 211/126.1
(58) Field of Search ................. 206/263, 363; 211/126.1, 297; 422/300

(56) References Cited

U.S. PATENT DOCUMENTS

| 5,169,116 A | * | 12/1992 | Bergtz ........................ 422/300 |
| 5,173,273 A | | 12/1992 | Brewer ....................... 422/300 |
| 5,215,726 A | | 6/1993 | Kudla et al. ................ 422/297 |
| 5,281,400 A | * | 1/1994 | Berry ......................... 422/300 |
| 5,284,632 A | | 2/1994 | Kudla et al. ................ 422/297 |
| 5,294,413 A | | 3/1994 | Riihimaki et al. .......... 422/297 |
| 5,346,677 A | * | 9/1994 | Risk ........................... 422/300 |
| 5,384,103 A | | 1/1995 | Miller ........................ 422/310 |
| 5,424,048 A | * | 6/1995 | Riley ......................... 422/300 |
| 5,433,929 A | | 7/1995 | Riihimaki et al. .......... 422/297 |
| 5,451,379 A | | 9/1995 | Bowlin, Jr. ................ 422/297 |
| 5,492,671 A | | 2/1996 | Krafft ........................ 422/297 |
| 5,505,916 A | | 4/1996 | Berry, Jr. .................... 422/300 |
| 5,525,314 A | * | 6/1996 | Huson ........................ 422/300 |

* cited by examiner

Primary Examiner—Robert J. Warden, Sr.
Assistant Examiner—Imad Soubra
(74) Attorney, Agent, or Firm—Woodbridge & Associates, P.C.; Richard C. Woodbridge; Stuart H. Nissim

(57) ABSTRACT

A sterilizable bracket (10) for supporting medical instruments (22) includes a resilient body (12) that surrounds and encapsulates a relatively rigid metal skeleton (14) which is attached to a plurality of studs (16) which secure the bracket (10) to a sterilizable tray (18). instruments (22) are received in indentations (24) in the resilient body (12). Each indentation (24) includes a plurality of ribs or fingers (28) which permit sterilizing steam to flow around the instruments (22). The resilient body (12) comprises a silicone material which encapsulates the skeleton backbone (14) which, in turn, gives the bracket (10) strength and flexibility. Threaded studs (16) having a slot (46) at one end and threads (50) at the other are employed to attach the bracket (10) to the sterilizable tray (18). The slot (46) in the head (44) of each of the studs (16) receives the metal skeleton backbone (14). Lock nuts (52) or the like are employed to secure the threaded portions (50) of the studs (16) in regularly spaced perforations (20) in the bottom of the sterilizable tray (18). The relatively rigid spring tempered skeleton backbone (14) includes a plurality of peaks (32) and valleys (30) oriented in such a way that they align with peaks (26) and indentations (24) of the resilient body (12) respectively. This structure (14) provides additional strength to the resilient silicone body (12).

11 Claims, 2 Drawing Sheets

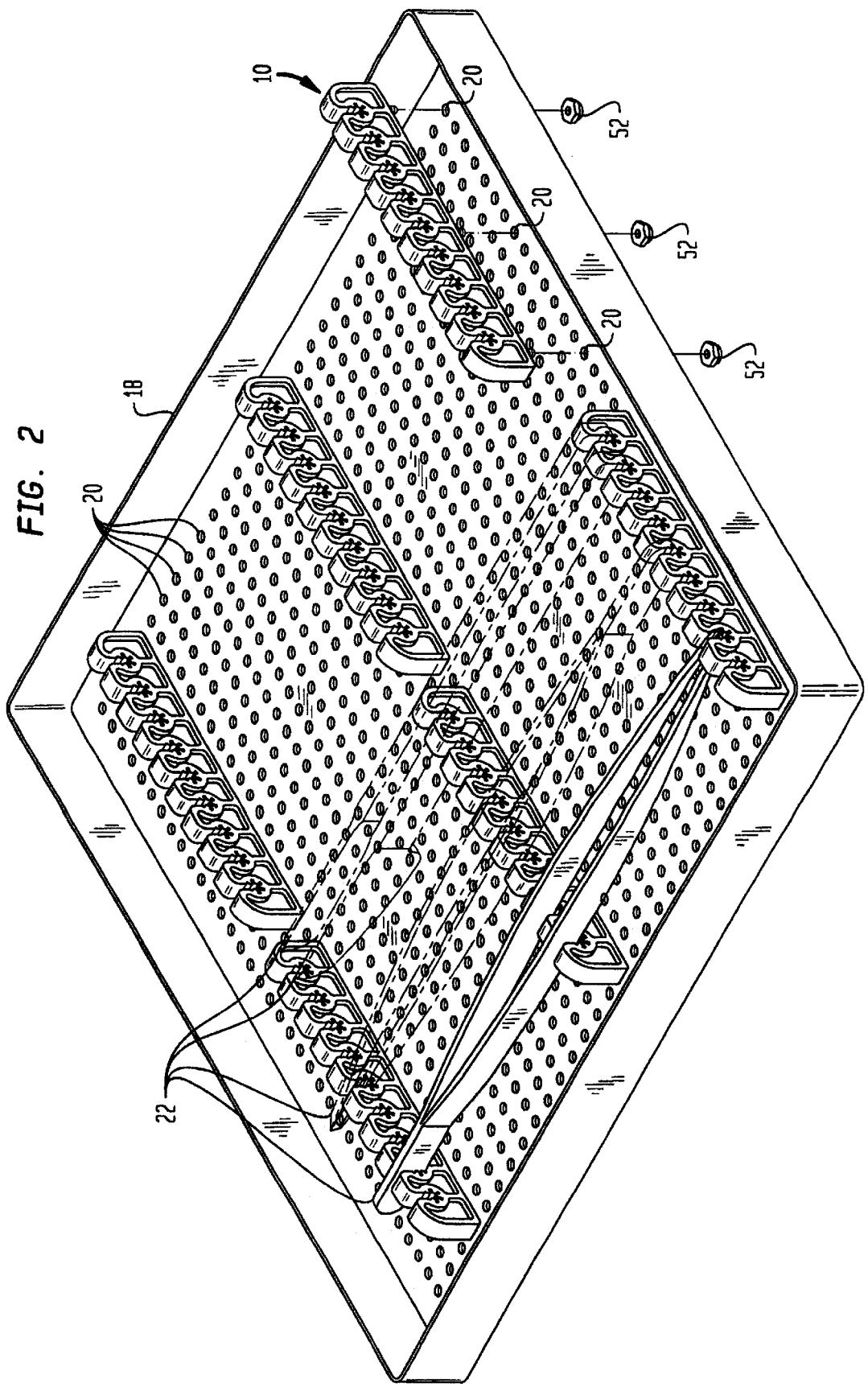

INSTRUMENT BRACKET FOR USE WITH A STERILIZABLE TRAY

BACKGROUND OF THE INVENTION

1. Field of the Invention

The invention comprises a bracket for supporting medical instruments in a sterilizable tray in which the bracket body is formed primarily from resilient silicone and is strengthened by a relatively rigid spring tempered metal interior skeleton backbone.

2. Description of Related Art

It is common practice to put medical instruments on trays and place them into high temperature environments for the purposes of sterilization. Steam heated autoclaves are probably the most common device used for killing germs and other biohazards. The instruments to be sterilized are generally placed in trays which, in turn, are placed into the cleansing environment In order to keep the instruments from moving, it is fairly common practice to separate and support them with brackets.

Instrument supporting brackets can take several different forms. Perhaps the most common form is a custom tray which includes custom made brackets laid out according to the specific request of the customer. An outline of the instrument to be supported is frequently printed on the bottom surface of the tray so that accurate instrument positioning is achieved. It is also common practice to place an English language legend, such as "Russian Tissue Forceps" adjacent to the outline of the desired instrument. The custom made brackets, which generally have an irregular shape, are then permanently attached to the tray with rivets. While such trays have advantages, they have several disadvantages too. First of all, they are expensive and time consuming to produce because each tray has to be individualized for each specific customer's request. Second, brackets are not removable and, therefore, there is no flexibility in the layout of the tray. Instrument holding trays, such as described are sold under the trademark MEDITRAY® by Case Medical, Inc., 65 Railroad Avenue, Ridgefield, N.J. 07657.

Another technique for attaching prior art brackets to a sterilizable tray is to have the brackets slide into a keyway that is provided for on the tray itself.

In an effort to further reduce costs, instrument holding brackets have recently become available which comprise stainless steel or aluminum bodies covered with a thin coat of nylon. The brackets typically have an L-shaped cross section. A pair of studs is attached to the bottom of the L-shaped bracket with nylon serving as the adhesive. The stainless steel or aluminum brackets just described can then be placed selectively or randomly on a tray having a plurality of regularly spaced perforations therein.

While the foregoing describe improvements in the art, they still do not present an optimal structure. What is desired is a bracket that will: withstand high temperatures; provide secure support for heavy. instruments, yet light support for delicate instrumentation; provide for complete surrounding by steam; provide for the ability to grab and securely hold heavy and delicate instruments; provide flexibility and strong support at the same time; and, also, provide for the ability to place brackets at a wide variety of locations in order to accommodate a wide spectrum of instruments.

It was in the context of the foregoing prior art and the above identified needs that the present invention arose.

SUMMARY OF THE INVENTION

Briefly described, the invention comprises a bracket for supporting medical instruments in a sterilizable tray in which the bracket body is formed primarily from resilient silicone and is strengthened by a relatively rigid metal interior skeleton backbone. The resilient silicone bracket body includes a plurality of medical instrument receiving indentations or valleys separated by intervening peaks. Resilient ribs formed in the instrument receiving indentations gently support the medical instruments and optimally allow sterilizing steam to be exposed to the maximum surface area of the instrument. The spring tempered stainless steel skeleton backbone is encapsulated by the silicone body. The skeleton also includes peaks and valleys that mimic and align with the peaks and valleys of the silicone body and provide additional strength thereto. Flow through holes or apertures in the skeleton backbone permit the silicone to optimally bond with the backbone. Threaded studs are mechanically attached to the skeleton backbone. Each stud includes a slotted head which attaches to the bottom edge of the stainless steel skeleton backbone, a widened, ring-like midsection, and a threaded end that is distal from the slotted end of the stud. The slotted end and most of the round midsection of the stud are also encapsulated in the silicone. The bracket is preferably attached to the tray by placing the threaded portions of the studs through the perforations in the tray and attaching them thereto with lock nuts.

The invention may be more fully understood by reference to the following drawings.

BRIEF DESCRIPTION OF THE DRAWINGS

FIG. 2 is a perspective view of the preferred embodiment of the invention illustrated in FIG. 1 shown in the process of being placed into a sterilizable tray and locked with respect thereto with lock nuts.

DETAILED DESCRIPTION OF THE INVENTION

During the course of this description like numbers will be used to identify like elements according to the different views that illustrate the invention.

Figure 1:
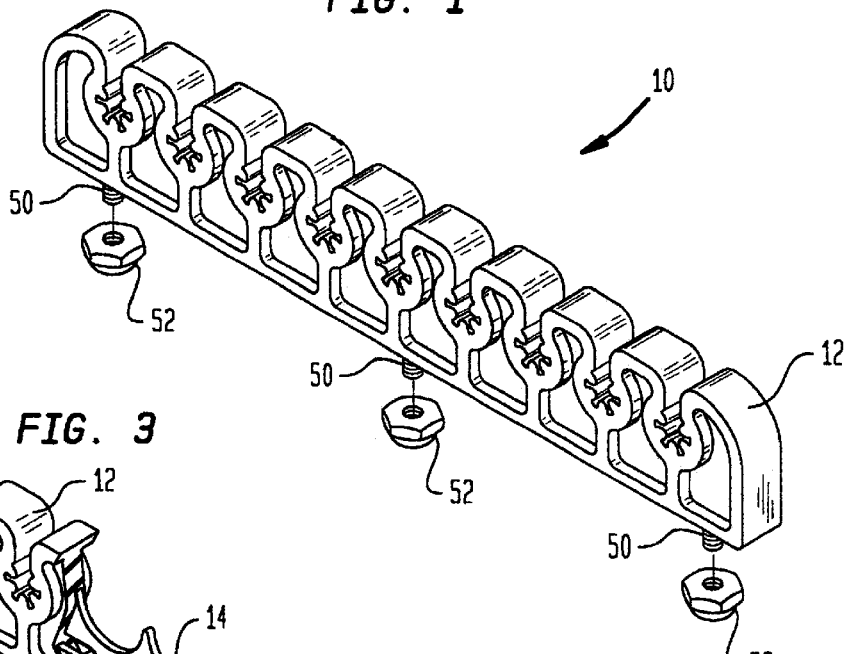
FIG. 1 is a perspective view of the preferred embodiment of the sterilizable instrument bracket.

The preferred embodiment of the invention 10 is illustrated in a perspective view in FIG. 1. The three major structural components of the preferred embodiment 10 are a resilient silicone body 12, a skeleton backbone 14 encapsulated by the silicone body 12 and a plurality of threaded studs 16 partially encapsulated by the silicone body 12.

Bracket 10 is preferably attached to a sterilizable tray 18 such as illustrated in FIG. 2. Tray 18 includes a plurality of regularly spaced perforations or apertures 20 for receiving the threaded sections 50 of studs 16 of bracket 10. The threaded section or end 50 of studs 16 pass through the perforations 20 and are locked with respect thereto by lock nuts 52 which threadably attach to the threaded portion 50 on the portion of stud 16 opposite from the silicone body 12. Alternate methods could also be employed to attach studs 16 to tray 18. For example, the threaded sections 50 of the studs 16 could be smooth or threaded and a push on clip could be used instead of lock nuts 52 to secure the bracket 10 to the apertures 20 in tray 18. A plurality of different medical instruments 22 are supported by brackets 10 as shown in FIG. 2. Threaded studs 16 are located at intervals identical to the spacing between perforations 20 in tray 18 so that the brackets 10 may be placed in any arrangement for supporting medical instruments 22. Therefore, it is easy to rearrange the brackets to accommodate a wide variety of different medical instruments 22 which may vary substantially in size, weight and shape.

Figure 3:
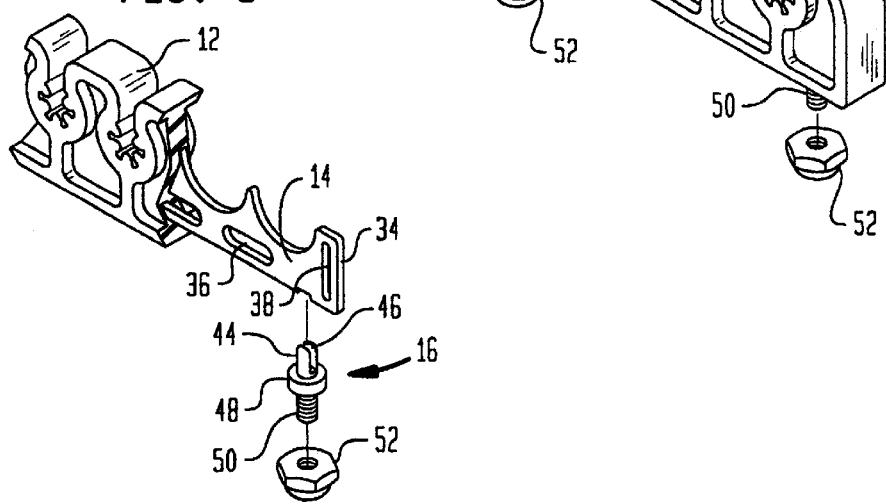
FIG. 3 is a partial, perspective cross sectional view of the bracket illustrated in FIG. 1 showing the manner in which the slotted head of the studs are attached to the relatively rigid spring tempered skeleton backbone.
Figure 4:
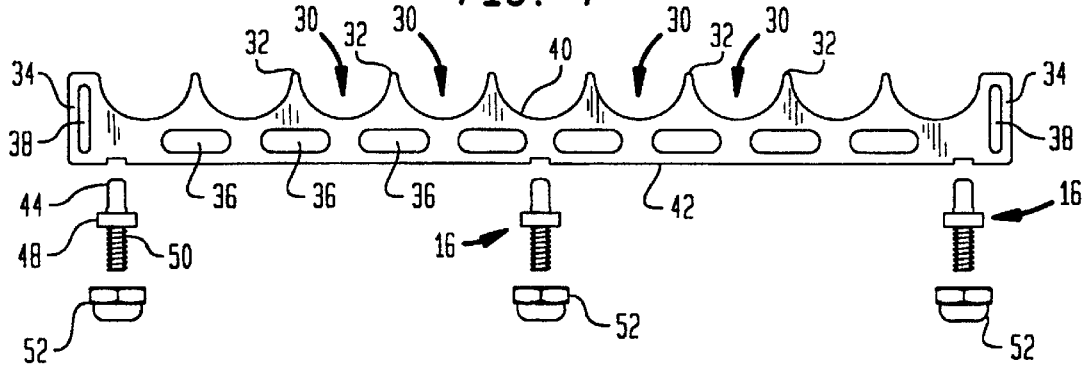
FIG. 4 is a front, exploded view illustrating the manner in which the attachment studs are connected to the skeleton backbone.
Figure 5:
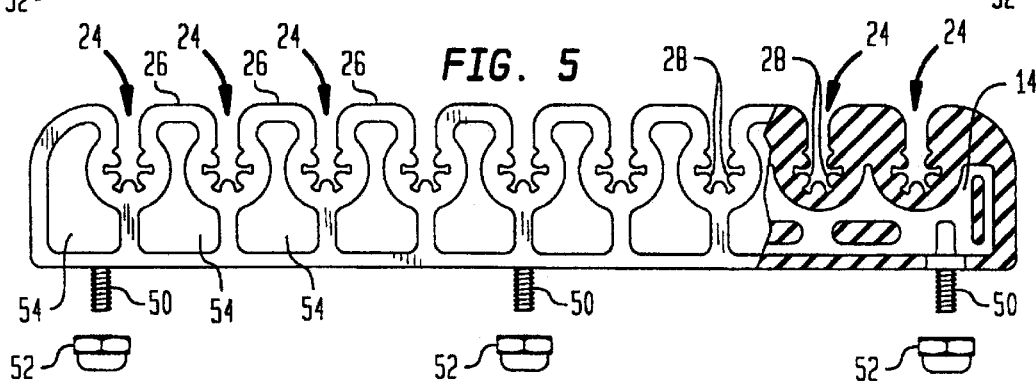
FIG. 5 is a partial, front cross sectional view of the fully assembled bracket.

Details of the silicone body 12, its related relatively rigid spring tempered skeleton backbone 14, and threaded support studs 16 will be more fully appreciated by referring to FIGS. 3–5.

Medical instruments 22 are received in indentations or valleys 24 in the resilient silicone body 12. The medical receiving indentations are separated by resilient peaks 26. Ribs 28 located at regular intervals inside of the instrument receiving indentations 24 provide gentle yet turn support for the medical instruments 22. More importantly, ribs 28 permit sterilizing steam to circulate in between so as to further assist in the killing of biohazardous germs and materials. There is a small gap between adjacent peaks 26 and the valleys 24 so as to further hold and secure an instrument 22 in the bracket 10.

The profile of the relatively rigid spring tempered stainless steel skeleton backbone 14 generally mimics the profile of the peaks 26 and valleys 24 of the resilient silicone body 12. Skeleton backbone 14, therefore, includes valleys 30 separated by peaks 32. Each skeleton backbone 14 also includes a top edge 40 which incorporates peaks 32 and valleys 30, a bottom edge 42 which is attached to studs 16, and a pair of side ends 34. Flow through apertures 36 are located along the length of skeleton backbone 14. Likewise a pair of flow through holes or apertures 38, oriented perpendicularly to flow through apertures 36, are located in the side ends 34 of skeleton backbone 14.

Each stud 16 includes a head 44, a ring shaped midsection 48 in the middle thereof, and a threaded end or section 50 distal from head 44. A skeleton receiving slot 46 is located in stud head 44, The slot 46 in stud head 44 is slightly smaller than the width of the skeleton backbone 14 so that it mechanically locks onto the bottom edge 42 of the skeleton backbone 14. For additional security it may be desirable to weld the slotted head 44 to the bottom edge 42 of the skeleton backbone 14. The ring shaped midsection 44 of stud 16 supports the bottom edge 42 of the skeleton backbone 14.

The bracket 10, according to its preferred embodiment, is constructed in the following 35 manner. First, the bottom edge 42 of the backbone 14 is placed into the slot 46 in the head 44 of stud 16. Three studs 16 are shown in FIGS. 1–5 but two studs 16 or four or more studs 16 could also be used according to the demands of the use. Studs 16 are preferably placed at regular intervals identical to the spacing between perforations 20 in tray 18 as previously described. Stud heads 44 are then mechanically attached to the bottom edge 42 of skeleton backbone 14 either by crimping or by welding, or both. Second, the skeleton backbone 14 with studs 16 attached is then placed into a mold in which silicone is injected to form resilient body 12. The silicone completely encapsulates the skeleton backbone 14. Flow through apertures 36 and 38 in skeleton backbone 14 further assist in mechanically anchoring the silicone body 12 to the skeleton backbone 14. As previously described, the silicone also encapsulates the head 44 and most of the midsection 48 of stud 16. The exposed portion of the midsection 48 of stud 16 also serves as a stop for the bracket 10 when it is placed in position on tray 18. The resulting molded silicone bracket 10 includes sculpted indents 54 in the sides of the silicone bracket body 12. Sculpted indents 54 help to conserve weight and space.

The invention described has several significant, nonobvious advantages over the prior art. First, it provides for substantial versatility for permanent or semi-permanent fixturing of brackets 10 with respect to instruments. Second, it provides important structural support for heavy instruments 22, yet protects delicate instruments 22. Third, the encapsulated metal 14 cannot damage delicate instrumentation 22. Fourth, the flexible silicone ribs 28 provide grip with minimal contact of the instrument 22 to the bracket surface, yet permits optimum sterilization. Presently existing prior art brackets do not allow for optimal sterilization as they tend to be bulky and grip a large surface area of the instrument 22. Fifth, the spring tempered metal skeleton 14 permits the bracket 10 to adjust slightly so that the threaded portion 50 of the studs 16 can align with perforations 20 in the tray 18 even if there isn't perfect spacing.

While the invention has been described with reference to the preferred embodiment thereof, it will be appreciate by those of ordinary skill in the art that modifications can be made to the structure and form of the invention without departing from the spirit and scope thereof.

What is claimed is:

1. A sterilizable instrument support bracket apparatus (10) for attachment to a tray (18) having a plurality of regularly spaced perforations (20) therein, said apparatus (10) comprising:

a skeleton means (14) comprising a metal strip (14);

stud means (16) attached to said skeleton means (14);

a resilient silicone body (12) substantially completely encapsulating said skeleton means (14); and, instrument support means (24) located on said resilient body (12) for supporting at least one medical instrument (22), said instrument support means comprising;

a plurality of instrument receiving indentations (24) in said resilient body which include silicone ribs (28) to improve the circulation of sterilizing steam around said medical instrument(22);

wherein said bracket apparatus (10) may be attached to said tray (18) by passing said stud means (16) through said perforations (20) and fastening said stud means (16) with respect thereto and wherein said skeleton means (14) permits said bracket (10) to adjust slightly so that the said stud means (16) can align with said perforation (20) in said tray (18) if the spacing between said perforations (20) is not precisely regular.

2. The apparatus of claim 1 wherein said stud means (16) each respectfully include a threaded section (50) thereon and wherein said studs (16) are attached to said tray (18) with threaded nuts (52) which mate with said threaded nuts (52) are lock nuts.

3. The apparatus of claim 2 wherein said threaded nuts (52) are lock nuts.

4. The apparatus of claim 1 wherein said strip (14) comprises a spring tempered metal strip (14) with apertures (36, 38) therein to permit silicone to flow therethrough in order to mechanically anchor said silicone body (12) to said flexible strip (14).

5. The apparatus of claim 4 wherein said spring tempered metal strip (14) includes a plurality of peaks (32) and valleys (30), wherein the valleys (30) of said flexible strip (14) are located adjacent to said instrument receiving indentations (24).

6. The apparatus of claim 5 wherein said studs (16) include a slotted head (44, 46) distal from the threaded section (50) thereof and wherein said spring tempered metal strip (14) is received in said slotted head (44, 46) and mechanically attached thereto.

7. The apparatus of claim 6 wherein said spring tempered metal strip (14) comprises a stainless steel strip (14).

8. The apparatus of claim 1 wherein said stud means (16) are attached to said tray (18) by a push on clip means.

9. A sterilizable instrument support bracket apparatus (10) for attachment to a tray (18) having a plurality of regularly spaced perforations (20) therein, said apparatus (10) comprising:

a skeleton means (14) comprising a metal strip (14);

stud means (16) attached to said skeleton means (14);

a resilient silicone body (12) substantially completely encapsulating said skeleton means (14); and, instrument support means (24) located on said resilient body (12) for supporting at least one medical instrument (22), said instrument support means (24) comprising at least one indentation (24) including a plurality of silicone ribs (28) located therein to improve the circulation of sterilizing steam around said medical instrument (22), wherein said bracket apparatus (10) may be attached to said tray (18) by passing said stud means (16) through said perforations (20) and fastening said stud means (16) with respect thereto, and wherein said skeleton means (14) permits said bracket (10) to adjust slightly so that the said stud means (16) can align with said perforations (20) in said tray (18) if the spacing between said perforations (20) is not precisely regular.

10. A sterilizable instrument support bracket apparatus (10) for attachment to a tray (18) having a plurality of regularly spaced perforations (20) therein, said apparatus (10) comprising:

a skeleton means (14) comprising a spring tempered metal strip (14) with apertures (36, 38) therein;

stud means (16) attached to said spring tempered metal strip (14);

a resilient silicone body (12) substantially completely encapsulating said spring tempered metal strip (14) and a portion of said stud means (16); and, instrument support means (24) integral with said resilient silicone body (12) and located on said resilient body (12) for supporting at least one medical instrument (22), wherein said bracket apparatus (10) maybe attached to said tray (18) by passing said portion of said stud means (16) that is outside of said resilient silicone body (12) through said perforations (20) and fastening said stud means (16) with respect thereto and further wherein said apertures (36, 38) in said spring tempered metal strip (14) permits silicone to flow there through during encapsulation of said skeleton means (14) in order to mechanically anchor said silicone body (12) to said spring tempered metal strip (14).

11. A sterilizable instrument support bracket apparatus (10) for attachment to a tray (18) having a plurality of regularly spaced perforations (20) therein, said apparatus (10) comprising:

a skeleton means (14) comprising a spring tempered metal strip (14);

stud means (16) attached to said spring tempered metal strip (14), said stud means (16) including a threaded section (50) and a slotted head (44, 46) distal from said threaded section (50) thereof such that said spring tempered metal strip (14) is received in said slotted head (44, 46) and mechanically attached thereto;

a resilient silicone body (12) substantially completely encapsulating said spring tempered metal strip (14) and a portion of said stud means (16); and, instrument support means (24) located on said resilient silicone body (12) and integral therewith for supporting at least one medical instrument (22), wherein said bracket apparatus (10) may be attached to said tray (18) by passing said threaded section (50) of said stud (16) through said perforations (20) and fastening said threaded section (50) to said tray (18) with threaded nuts (52) which mate with said threaded sections (50).

* * * * *